United States Patent
Kumar et al.

(10) Patent No.: US 10,828,446 B2
(45) Date of Patent: Nov. 10, 2020

(54) INSULATED ENDOTRACHEAL DEVICES AND SYSTEMS FOR TRANSPULMONARY THERMAL TRANSFER

(71) Applicant: Mayo Foundation For Medical Education and Research, Rochester, MN (US)

(72) Inventors: Matthew M. Kumar, Austin, MN (US); Larry Dale Johnson, Red Wing, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1242 days.

(21) Appl. No.: 15/021,138

(22) PCT Filed: Sep. 12, 2014

(86) PCT No.: PCT/US2014/055349
§ 371 (c)(1),
(2) Date: Mar. 10, 2016

(87) PCT Pub. No.: WO2015/038870
PCT Pub. Date: Mar. 19, 2015

(65) Prior Publication Data
US 2016/0213870 A1    Jul. 28, 2016

Related U.S. Application Data

(60) Provisional application No. 61/877,125, filed on Sep. 12, 2013.

(51) Int. Cl.
*A61M 16/04* (2006.01)
*A61M 11/00* (2006.01)
(Continued)

(52) U.S. Cl.
CPC ........... *A61M 16/0486* (2014.02); *A61F 7/12* (2013.01); *A61M 11/00* (2013.01);
(Continued)

(58) Field of Classification Search
CPC .. A61M 11/00; A61M 16/00; A61M 16/0057; A61M 16/04; A61M 16/0409;
(Continued)

(56) References Cited

U.S. PATENT DOCUMENTS 3,438,375 A * 4/1969 Ericson ............. A61M 25/1002
604/268
3,848,617 A * 11/1974 Dray ..................... A61M 16/12
137/88

(Continued)

FOREIGN PATENT DOCUMENTS

EP    0246176 A2    11/1987
EP    1731118 A1    12/2006
(Continued)

OTHER PUBLICATIONS

Abramson et al., "Neurologic recovery after cardiac arrest: effect of duration of ischemia," *Brain Resuscitation Clinical Trial I Study Group. Crit. Care Med.*, 1985; 13(11):930-1.
(Continued)

*Primary Examiner* — Justine R Yu
*Assistant Examiner* — Mathew D Ziegler
(74) *Attorney, Agent, or Firm* — Mueting Raasch Group

(57) ABSTRACT

Endotracheal devices, systems, and methods of using the same for transpulmonary thermal transfer to, e.g., induce transpulmonary hypothermia and/or warming. The endotracheal devices may include first and second lumens extending through the endotracheal device along with insulation
(Continued)

located in an interior of the tube of the endotracheal device to limit thermal energy transfer between fluids in the first and second lumens.

9 Claims, 5 Drawing Sheets

(51) Int. Cl.
| | |
|---|---|
| *A61M 16/10* | (2006.01) |
| *A61M 16/14* | (2006.01) |
| *A61F 7/12* | (2006.01) |
| *A61M 16/20* | (2006.01) |
| *A61F 7/00* | (2006.01) |
| *A61B 18/00* | (2006.01) |

(52) U.S. Cl.
CPC ...... *A61M 16/042* (2014.02); *A61M 16/0434* (2013.01); *A61M 16/0463* (2013.01); *A61M 16/1075* (2013.01); *A61M 16/14* (2013.01); *A61M 16/208* (2013.01); *A61B 2018/00101* (2013.01); *A61F 2007/0063* (2013.01); *A61F 2007/0069* (2013.01); *A61F 2007/0091* (2013.01); *A61F 2007/126* (2013.01); *A61M 2205/3368* (2013.01); *A61M 2205/3633* (2013.01)

(58) Field of Classification Search
CPC ............ A61M 16/0418; A61M 16/042; A61M 16/0434; A61M 16/044; A61M 16/0463; A61M 16/0486; A61M 16/0488; A61M 16/1075; A61M 16/14; A61M 16/20; A61M 16/208; A61M 2205/07; A61M 2205/3368; A61M 2205/36; A61M 2205/3633; A61M 25/00; A61M 25/10; A61M 2025/0004; A61M 2025/0043; A61M 2025/0045; A61M 39/00; A61M 39/08; A61M 39/22; A61M 39/24; A61M 2039/082; A61B 2018/00053; A61B 2018/00059; A61B 2018/00089; A61B 2018/00101; A61B 2018/00166; A61B 1/267–2676; A61F 7/12; A61F 2007/0063; A61F 2007/0069; A61F 2007/0091; A61F 2007/126
See application file for complete search history.

(56) References Cited

U.S. PATENT DOCUMENTS

| | | | | |
|---|---|---|---|---|
| 4,248,234 A * | 2/1981 | Assenza | ............ | A61M 25/0054 604/170.01 |
| 5,063,921 A * | 11/1991 | Howe | ............ | A61M 16/16 128/200.14 |
| 5,067,497 A * | 11/1991 | Greear | ............ | A61M 16/04 128/207.15 |
| 5,167,622 A * | 12/1992 | Muto | ............ | A61M 16/0463 604/35 |
| 5,353,783 A * | 10/1994 | Nakao | ............ | A61B 1/00135 600/106 |
| 6,224,570 B1 * | 5/2001 | Le | ............ | A61B 17/32037 604/165.02 |
| 6,443,156 B1 * | 9/2002 | Niklason | ............ | A61M 16/04 128/207.14 |
| 6,983,749 B2 | 1/2006 | Kumar et al. | | |
| 7,201,168 B2 * | 4/2007 | McGrail | ............ | A61M 16/04 128/207.14 |
| 9,687,621 B2 * | 6/2017 | Hoftman | ............ | A61M 16/0816 |
| 2002/0189618 A1 * | 12/2002 | Augustine | ............ | A61B 1/267 128/207.15 |
| 2007/0017527 A1 * | 1/2007 | Totz | ............ | A61M 16/04 128/207.15 |
| 2008/0029100 A1 * | 2/2008 | Glassenberg | ............ | A61B 1/04 128/207.15 |
| 2009/0107503 A1 | 4/2009 | Baran | | |
| 2010/0147309 A1 * | 6/2010 | Cuevas | ............ | A61M 16/04 128/207.14 |
| 2012/0000471 A1 * | 1/2012 | Harrington | ............ | A61M 16/04 128/207.15 |
| 2012/0080031 A1 | 4/2012 | Belson | | |
| 2012/0167882 A1 * | 7/2012 | Wood | ............ | A61B 1/00082 128/204.17 |
| 2012/0259206 A1 | 10/2012 | Roberts et al. | | |
| 2013/0096379 A1 | 4/2013 | Goldberg | | |
| 2014/0350648 A1 * | 11/2014 | Ericson | ............ | A61M 16/04 607/105 |

FOREIGN PATENT DOCUMENTS

| | | |
|---|---|---|
| EP | 1153627 B1 | 11/2007 |
| GB | 2397229 A | 7/2004 |
| WO | WO 02/47748 A1 | 6/2002 |
| WO | WO 03/026721 A2 | 4/2003 |
| WO | WO 2010/065616 A1 | 6/2010 |
| WO | WO 2013/087845 A1 | 6/2013 |
| WO | WO 2015/038870 A1 | 3/2015 |

OTHER PUBLICATIONS

Bernard et al., "Treatment of comatose survivors of out-of-hospital cardiac arrest with induced hypothermia," *N Engl. J. Med.*, Feb. 21, 2002; 346(8):557-63.

Clifton et al., "Lack of Effect of Induction of Hypothermia after Acute Brain Injury," *N Engl. J. Med.*, Feb. 22, 2001; 344(8): 556-63.

D'Cruz et al., "Hypothermic Reperfusion After Cardiac Arrest Augments Brain-Derived Neurotrophic Factor Activation," *J. Cereb. Blood Flow Metab.*, 2002; 22(7):848-51.

Hicks et al., "Hypothermia During Reperfusion After Asphyxial Cardiac Arrest Improves Functional Recovery and Selectively Alters Stress-Induced Protein Expression," *J. Cereb. Blood Flow Metab.*, 2000; 20(3):520-30.

Horn et al., "Global cerebral ischemia and subsequent selective hypothermia," *Acta Neuropathol.*, 1991; 81:443-9.

International Preliminary Report on Patentability dated Mar. 15, 2016, for International Application No. PCT/US2014/055349, 13 pgs.

International Search Report and International Written Opinion dated Dec. 16, 2014, for International Application No. PCT/US2014/055349, 19 pgs.

Janata et al., "Hypothermia After Cardiac Arrest," *Prog. Cardiovasc. Dis.*, 2009; 52(2):168-79.

Kochanek et al., "Therapeutic Hypothermia for Severe Traumatic Brain Injury," *JAMA*, Jun. 11, 2003; 289(22):3007-9.

Krieger et al., "Therapeutic Hypothermia for Acute Ischemic Stroke: What Do Laboratory Studies Teach Us?" *Stroke*, Jun. 2004; 35(6):1482-9.

Nolan et al., "Therapeutic Hypothermia After Cardiac Arrest," *Circulation*, Jul. 8, 2003; 108:118-21.

Rosomoff et al., "Cerebral Blood Flow and Cerebral Oxygen Consumption During Hypothermia," *Am. J. Physiol.*, Oct. 1954;179(1):85-8.

Safar et al., "Therapeutic hypothermia after cardiac arrest," *N. Engl. J. Med.*, Feb. 21, 2002; 346(8):612-3.

Sakas et al., "Lack of Effect of Induction of Hypothermia after Acute Brain Injury," *N. Engl. J. Med.*, Jul. 5, 2001; 345(1):66.

Shiozaki et al., "Effect of mild hypothermia on uncontrollable intracranial hypertension after severe head injury," *J. Neurosurg.*, Sep. 1993; 79(3):363-8.

Sterz et al., "Mild hypothermic cardiopulmonary resuscitation improves outcome after prolonged cardiac arrest in dogs," *Crit. Care Med.*, Mar. 1991;19(3):379-89.

The Hypothermia after Cardiac Arrest Study Group, "Mild therapeutic hypothermia to improve the neurologic outcome after cardiac arrest," *N. Engl. J. Med.*, Feb. 21, 2002; 346(8):549-56.

(56) References Cited

OTHER PUBLICATIONS

Weinrauch et al., "Beneficial effect of mild hypothermia and detrimental effect of deep hypothermia after cardiac arrest in dogs," *Stroke*, Oct. 1992; 23(10):1454-62.

Zhang et al., "Initiation time of post-ischemic hypothermia on the therapeutic effect in cerebral ischemic injury," *Neurol. Res.*, May 2009; 31(4):336-9.

* cited by examiner

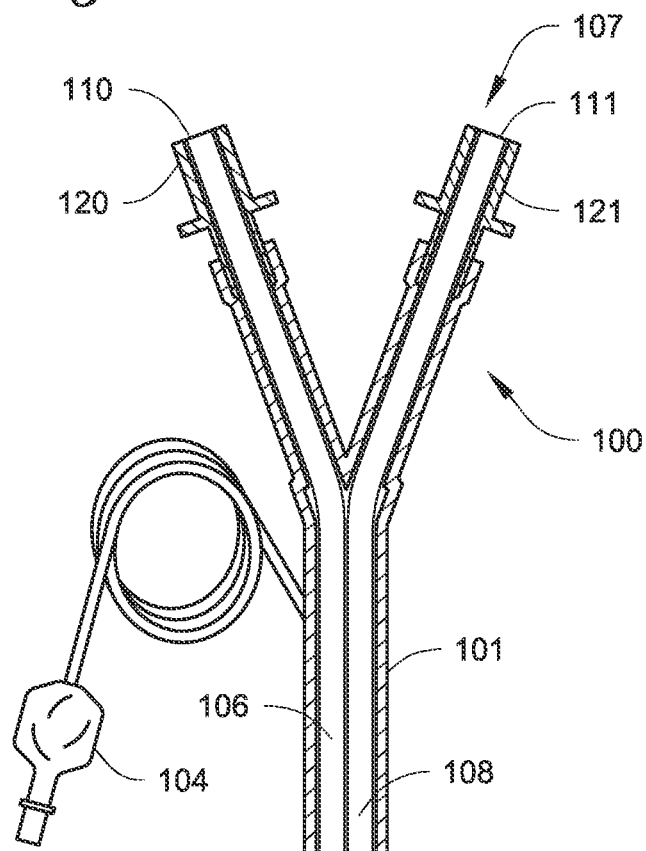
Fig. 1A
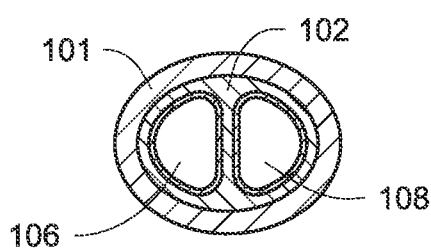
Fig. 1B
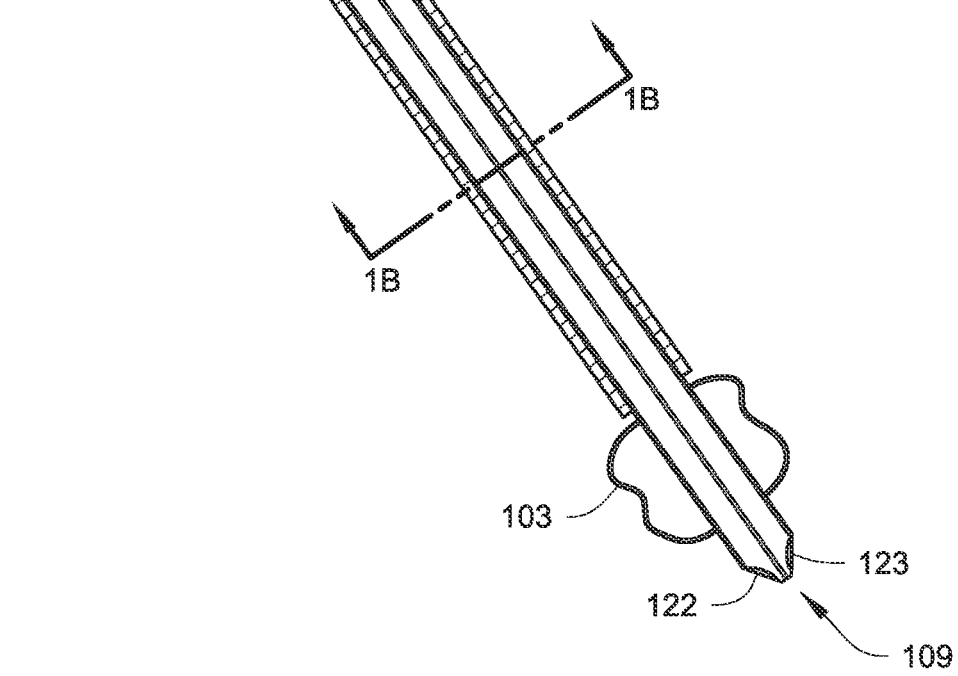

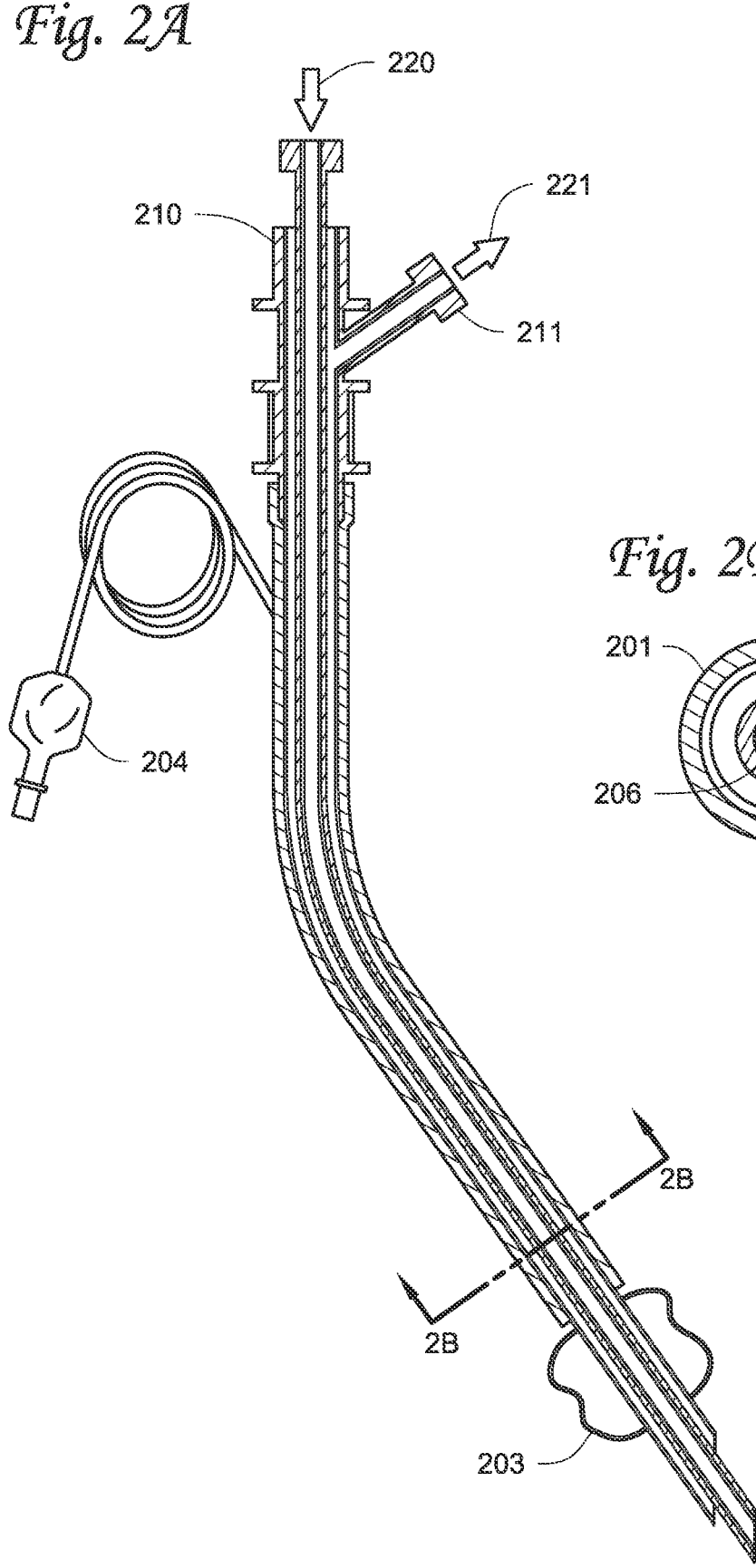

INSULATED ENDOTRACHEAL DEVICES AND SYSTEMS FOR TRANSPULMONARY THERMAL TRANSFER

RELATED APPLICATION

The present application is a U.S. National Stage Application of International Application PCT/US2014/055349, titled INSULATED ENDOTRACHEAL DEVICES AND SYSTEMS FOR TRANSPULMONARY THERMAL TRANSFER, filed on Sep. 12, 2014 which, claims the benefit under 35 U.S.C. § 119(e) of U.S. Provisional Patent Application No. 61/877,125, filed on Sep. 12, 2013 and titled INSULATED ENDOTRACHEAL DEVICES AND SYSTEMS FOR TRANSPULMONARY THERMAL TRANSFER, which is hereby incorporated by reference in its entirety.

GOVERNMENT LICENSE RIGHTS

This invention was made with government support under W81XWH-11-2-0134 awarded by the U.S. Army. The government has certain rights in the invention.

Endotracheal devices, systems, and methods of using the same for transpulmonary thermal transfer to, e.g., induce transpulmonary hypothermia and/or warming are described herein.

BACKGROUND

Hypothermia protects cells from ischemia Moderate hypothermia (28-32° C.) has been used successfully during open-heart surgeries over the past half century to prevent ischemic injury to vital organs Animal studies have shown improved neurological outcome when hypothermia was induced following cardiac arrest and return of spontaneous circulation. Recent randomized clinical trials from Europe and Australia confirm the beneficial effects of therapeutic hypothermia on comatose survivors of out-of-hospital cardiac arrest.

Several mechanisms by which hypothermia brings about beneficial effects have been reported. The cerebral metabolic rate of oxygen (CMRO2) decreases by about 6-7% per 1° C. drop in brain temperature. Around 32-34° C., the beneficial effects of hypothermia are realized while the negative effects, such as arrhythmia, coagulopathy and increased propensity for infection, are minimized. Hypothermia significantly diminishes the magnitude of neuronal apoptosis, reduces the formation of free radicals and excitatory neurotransmitters, preserves the integrity of the blood-brain barrier and decreases intracranial pressure. The therapeutic window for hypothermia after middle cerebral artery occlusion is 10-30 minutes for the basal ganglia and 30-60 minutes for the cerebral cortex. No effect on infarct volume is observed if hypothermia is delayed over 1 hour after the start of ischemia. Biochemical markers of ischemia are less pronounced when induction of hypothermia is begun within 60 minutes of the injury. It is well recognized in humans that the upper limit for recovery from anoxia under normothermic conditions is 5-7 minutes and that after 12-14 minutes of anoxia brain death is inevitable. Hence, time is of the essence if the beneficial effects of hypothermia are to be realized following ischemic injury to the brain.

Clinical and laboratory studies show cell preservation is best achieved when hypothermia can be induced prior to, or soon after, the onset of ischemia. However, the current methods to induce hypothermia are inefficient, unreliable, too slow or highly invasive. Lack of safe and reliable technology to induce hypothermia has been a limiting factor to the widespread use of therapeutic hypothermia. Body surface cooling methods are inefficient, slow and unpredictable. Peritoneal cooling is rapid but fraught with potential complications and generally not favored by physicians. Extracorporeal cooling is rapid and predictable but shortcomings include the need for surgical vascular access and anticoagulation, the potential for bleeding, the possibility of infection, and the difficult logistics of running the apparatus. Several intravascular cooling devices are currently being evaluated but preliminary results show that they are not efficient heat transfer tools and share the same pitfalls of extracorporeal devices. More recently, spraying volatile liquids into the nasopharynx has been purported induce hypothermia of the brain following cardiac arrest. There are several drawbacks to this technology. It is slow and inefficient. It does not provide hypothermia to protect other vital organs.

SUMMARY

Endotracheal devices, systems, and methods of using the same for transpulmonary thermal transfer to, e.g., induce transpulmonary hypothermia and/or warming are described herein.

To induce hypothermia and warming at an efficacious rate, the present invention achieves a larger thermal gradient across the alveolar membrane through insulation of the airway device and separation of the inspired and expired gases. The larger the thermal gradient across the alveolar membrane, faster the rate of systemic cooling or heating. In order to achieve this larger thermal gradient across the alveolar membrane, cooled or heated respiratory gases must be delivered in a manner that limits thermal energy transfer between inspiratory and expiratory gases during delivery. The endotracheal devices and methods described herein may, in one or more embodiments, produce an increased rate of cooling (or heating, if desired) by limiting thermal energy transfer between the fluids traveling through the device.

In one or more embodiments, the method may utilize: lungs for heat exchange, cooled gases for ventilation, helium or other inert gases to augment thermal conduction, and atomized phase change material such as liquid perfluorocarbons to achieve evaporative cooling from the lungs. The large surface area of the pulmonary alveoli is utilized to exchange heat from the blood to the inspired gases. In contrast to skin surface area of 1.8 m2, the lung alveolar surface area is 75 m2. In the lungs, blood comes in close proximity to the inspired gases, being separated by the alveolar membrane which is only a few microns in thickness, in contrast to 2-4 mm thickness of the human skin. The gossamer thinness of the alveolar membrane and the large surface area of the lungs are ideally suited for heat exchange. This heat loss is further enhanced by lowering the temperature of the inspired gases. As per the laws of thermodynamics, the heat exchange between the blood in the lung alveoli and the inspired gases is directly proportional to the temperature difference between them.

Helium may, in one or more embodiments, be added to the inspired gas mixture to improve the rate of heat transfer. The thermal conductivity and thermal diffusivity of helium is much greater than other biologically compatible gases such as oxygen, nitrogen, or carbon dioxide. As a result, more of the inspired gases equalize with the body temperature within the duration of each breath. This results in greater heat loss from the body than is otherwise possible with air or other gas mixtures.

In one or more embodiments, the heat loss from the lungs may be intensified by the addition of perfluorocarbon mist or other phase change material to the inspired gases. The phase change from liquid to vapor, or solid to liquid, extracts a significant amount of heat from the lungs due to the latent heat of vaporization. Since the heat transfer rate between the walls of the tracheobronchial tree and the droplets of phase change material is increased by helium, heliox and the phase change material work synergistically to amplify heat loss from the lungs.

The insulation provided in one or more embodiments of the endotracheal devices described herein may be arranged either inside or the outside of the conduit in the airway device through which the respiratory gases and liquids flow to and from the lungs. The insulation may, in one or more embodiments, restrict the transfer of thermal energy to and from the fluids within the conduit and the surrounding tissues or the ambient environment. The conduit and the insulation are, in one or more embodiments, flexible. The insulation element may, in one or more embodiments, be in the form of paint, foam, concentric sheets, or enclosed cells, ranging in thickness from a few microns to several millimeters. The insulation may, in one or more embodiments, be made of any biologically inert material such as polypropylene, polyurethane, or polyethylene. The interior of the conduit or the first layer or the outer layer of external insulation may, in one or more embodiments, be painted with reflective material so as to minimize radiant heat loss or heat gain by fluids within the conduit. The entire length of the conduit in the airway may, in one or more embodiments, be insulated.

In one configuration, the airway device has two or more separate conduits for the flow of inspired and expired gases and fluids. The objective is to minimize the mixing of inspired and expired gases within the airway device. One or more conduits carry the inspired gases and liquids and the other conduits carry the expired gases. The lumens of the conduits may, in one or more embodiments, be located side by side, or, in one or more embodiments, there may be one smaller inner tube located within one larger outer tube, or there may be two tubes with larger lumens and one tube with a smaller lumen located within a larger tube (the smaller tube may be used for continuous or intermittent insufflation of fluids and gases, with the larger tubes used for inspiratory and expiratory gases).

In one configuration, there may be unidirectional flow valves coupled to the entrance of the inspiratory limb and/or a unidirectional valve coupled to the exit of the expiratory limb of the airway device. The use of one or more unidirectional valves may, in one or more embodiments, limit or prevent mixing of the inspired and expired gases, and may also limit or prevent the blowback of any phase change material vapors into the inspiratory limb.

In one aspect, one or more embodiments of an endotracheal device described herein is configured for insertion through a tracheal passage to the bronchial bifurcation, the endotracheal device comprising a tube extending between a proximal end and a distal end, wherein the distal end of the endotracheal device is configured for placement proximate the bronchial bifurcation. The endotracheal device further includes: a first lumen extending through the endotracheal device, the first lumen extending from a first internal port to a first external port, wherein the first external port is proximate the proximal end of the endotracheal device and configured for attachment to a gas transfer apparatus, wherein the first external port is positioned outside of the tracheal passage when the first internal port is positioned proximate the bronchial bifurcation; a second lumen extending through the endotracheal device, the second lumen extending from a second internal port to a second external port, wherein the second external port is proximate the proximal end of the endotracheal device and configured for attachment to a gas transfer apparatus, wherein the second external port is positioned outside of the tracheal passage when the second internal port is positioned proximate the bronchial bifurcation; and insulation located in an interior of the tube of the endotracheal device, the insulation being located between the first lumen and the second lumen to limit thermal energy transfer between fluids located in the first and second lumens; wherein the first lumen is separate and independent of the second lumen such that gas passing through the first lumen cannot enter the second lumen between the first external port and the first internal port.

In one or more embodiments of the endotracheal devices described herein, the first lumen comprises an external surface located inside of the tube of the endotracheal device, and wherein the insulation comprises an insulation layer located on the external surface of the first lumen. In one or more embodiments, the second lumen comprises an external surface located inside of the tube of the endotracheal device, and wherein the insulation comprises an insulation layer located on the external surface of the second lumen.

In one or more embodiments of the endotracheal devices described herein, the first lumen comprises an external surface located inside of the second lumen, and wherein the insulation comprises an insulation layer located on the external surface of the first lumen.

In one or more embodiments of the endotracheal devices described herein, the insulation comprises tube insulation located on an external surface of the tube of the endotracheal device.

In one or more embodiments of the endotracheal devices described herein, the insulation comprises a chamber located in an interior of the tube of the endotracheal device, the chamber being located between the first lumen and the second lumen and configured to limit thermal energy transfer between fluids located in the first and second lumens. In one or more embodiments, the chamber comprises a vacuum port proximate the proximal end of the endotracheal device and configured for attachment to a vacuum device, wherein the vacuum port is positioned outside of the tracheal passage when the second internal port is positioned proximate the bronchial bifurcation, and wherein the chamber comprises a structure configured to retain a space between the first lumen and the second lumen when the chamber is held below atmospheric pressure. In one or more embodiments, the chamber comprises an inflatable chamber comprising a delivery configuration and an expanded configuration, and wherein the chamber provides more space between the first lumen and the second lumen in the expanded configuration than the delivery configuration. In one or more embodiments, the endotracheal device comprises an inflatable cuff positioned on an exterior of the tube, wherein the inflatable cuff is proximate the distal end of the endotracheal device, wherein the inflatable cuff comprises a collapsed configuration and an inflated configuration, wherein the inflatable cuff comprises a larger radial dimension in the inflated configuration than in the collapsed configuration where the radial dimension is measured radially outward from a longitudinal axis extending between the proximal end and the distal end of the tube, and wherein the inflatable cuff is in fluid communication with the chamber such that when the chamber is in the delivery configuration, the inflatable cuff is in the collapsed configuration and when the chamber is in the expanded configuration the inflatable cuff is in the inflated configuration.

In one or more embodiments of the endotracheal devices described herein, the endotracheal device comprises a third lumen extending from a third external port to an atomizing nozzle that is configured to deliver atomized fluid into the first lumen or the second lumen.

In one or more embodiments of the endotracheal devices described herein, the endotracheal device comprises a third lumen extending from a third external port to an atomizing nozzle that is configured to deliver atomized fluid to the bronchial bifurcation.

In one or more embodiments of the endotracheal devices described herein, the first lumen comprises a first one-way valve configured to allow inspiratory flow through the first lumen from the first external port to and out of the first internal port and limit expiratory flow through the first lumen from the first internal port to and out of the first external port. In one or more embodiments, the first one-way valve is located in the first lumen closer to the first internal port than the first external port. In one or more embodiments, the first one-way valve is located in the first lumen closer to the first external port than the first internal port. In one or more embodiments, the endotracheal device comprises a third lumen extending from a third external port to an atomizing nozzle that is configured to deliver atomized fluid into the first lumen. In one or more embodiments, the endotracheal device comprises a third lumen extending from a third external port to an atomizing nozzle that is configured to deliver atomized fluid to the bronchial bifurcation.

In one or more embodiments of the endotracheal devices described herein, the second lumen comprises a second one-way valve configured to allow expiratory flow through the second lumen from the second internal port to and out of the second external port and limit inspiratory flow through the second lumen from the second external port to and out of the second internal port. In one or more embodiments, the second one-way valve is located in the second lumen closer to the second external port than the second internal port. In one or more embodiments, the second one-way valve is located in the second lumen closer to the second internal port than the second external port.

In one or more embodiments of the endotracheal devices described herein, the insulation comprises an R value of 3 or higher.

In one or more embodiments of the endotracheal devices described herein, the insulation is configured to limit thermal energy transfer between a first fluid passing through the first lumen and a second fluid passing through the second lumen in the opposite direction such that the temperature of the first fluid does not change by more than 2.0 degrees C. when the first fluid and the second fluid are passing through each of the first and second lumens at flow rates of 50 liters per minute when the first and second fluids passing through the first and second lumens consist essentially of breathable gases and vapors.

In another aspect, one or more embodiments of a method of delivering transpulmonary thermal transfer are described herein, the method including: placing a distal end of an endotracheal device proximate the bronchial bifurcation by passing the distal end through a tracheal passage leading to the lung, the endotracheal device comprising a tube extending from the distal end to a proximal end located outside of the tracheal passage when the distal end is proximate the bronchial bifurcation; passing a first fluid to the bronchial bifurcation through a first internal port of a first lumen extending through the endotracheal device, the first lumen extending from the first internal port to a first external port, wherein the first external port is positioned outside of the tracheal passage proximate the proximal end of the endotracheal device, and wherein the first fluid passing through the first internal port to the bronchial bifurcation comprises a first temperature; removing at least a portion of the first fluid from the trachea proximate the bronchial bifurcation through a second internal port of a second lumen extending through the endotracheal device, the second lumen extending from the second internal port to a second external port, wherein the second external port is positioned outside of the tracheal passage proximate the proximal end of the endotracheal device, and wherein the first fluid passing through the second internal port from the trachea proximate the bronchial bifurcation comprises a second temperature different than the first temperature; and insulating the first lumen from the second lumen by providing insulation between the first lumen and the second lumen; wherein the first lumen is separate and independent of the second lumen such that the first fluid passing through the first lumen cannot enter the second lumen between the first external port and the first internal port.

In one or more embodiments of the methods described herein, the first lumen comprises an external surface located inside of the tube of the endotracheal device, and wherein the insulation comprises an insulation layer located on the external surface of the first lumen. In one or more embodiments, the second lumen comprises an external surface located inside of the tube of the endotracheal device, and wherein the insulation comprises an insulation layer located on the external surface of the second lumen.

In one or more embodiments of the methods described herein, the first lumen comprises an external surface located inside of the second lumen, and wherein the insulation comprises an insulation layer located on the external surface of the first lumen.

In one or more embodiments of the methods described herein, the method further comprises delivering an atomized second fluid into the first fluid passing through the first lumen.

In one or more embodiments of the methods described herein, the method further comprises delivering an atomized second fluid into the trachea proximate the bronchial bifurcation outside of the first fluid.

In one or more embodiments of the methods described herein, the first lumen comprises a first one-way valve configured to allow flow of the first fluid through the first lumen from the first external port to and out of the first internal port and limit reverse flow of the first fluid through the first lumen from the first internal port to and out of the first external port.

In one or more embodiments of the methods described herein, the second lumen comprises a second one-way valve configured to allow flow of the first fluid through the second lumen from the second internal port to and out of the second external port and limit reverse flow through the second lumen from the second external port to and out of the second internal port.

In another aspect, one or more embodiments of an endotracheal device described herein is configured for insertion through a tracheal passage to a location proximate the bronchial bifurcation, the endotracheal device comprising a tube extending between a proximal end and a distal end, wherein the distal end of the endotracheal device is configured for advancement to a location proximate the bronchial bifurcation through the tracheal passage. The endotracheal device includes: a first lumen extending through the endotracheal device, the first lumen extending from a first internal port to a first external port, wherein the first external port is proximate the proximal end of the endotracheal device and configured for attachment to a gas delivery apparatus, wherein the first external port positioned outside of the tracheal passage when the first internal port is positioned proximate the bronchial bifurcation; a second lumen extending through the endotracheal device, the second lumen extending from a second internal port to a second external port, wherein the second external port is proximate the proximal end of the endotracheal device and configured for attachment to a gas delivery apparatus, wherein the second external port is positioned outside of the tracheal passage when the second internal port is positioned proximate the bronchial bifurcation; and a chamber located in an interior of the tube of the endotracheal device, the chamber being located between the first lumen and the second lumen and configured to limit thermal energy transfer between fluids located in the first and second lumens; wherein the first lumen is separate and independent of the second lumen such that gas passing through the first lumen cannot enter the second lumen between the first external port and the first internal port.

In one or more embodiments of the endotracheal devices including a chamber as described herein, the chamber comprises a vacuum port proximate the proximal end of the endotracheal device and configured for attachment to a vacuum device, wherein the vacuum port is positioned outside of the tracheal passage when the second internal port is positioned proximate the bronchial bifurcation, and wherein the chamber comprises a structure configured to retain a space between the first lumen and the second lumen when the chamber is held below atmospheric pressure.

In one or more embodiments of the endotracheal devices including a chamber as described herein, the chamber comprises an inflatable chamber comprising a delivery configuration and an expanded configuration, and wherein the chamber provides more space between the first lumen and the second lumen in the expanded configuration than the delivery configuration. In one or more embodiments, the endotracheal device comprises an inflatable cuff positioned on an exterior of the tube, wherein the inflatable cuff is proximate the distal end of the endotracheal device, wherein the inflatable cuff comprises a collapsed configuration and an inflated configuration, wherein the inflatable cuff comprises a larger radial dimension in the inflated configuration than in the collapsed configuration where the radial dimension is measured radially outward from a longitudinal axis extending between the proximal end and the distal end of the tube, and wherein the inflatable cuff is in fluid communication with the chamber such that when the chamber is in the delivery configuration, the inflatable cuff is in the collapsed configuration and when the chamber is in the expanded configuration the inflatable cuff is in the inflated configuration.

In one or more embodiments of the endotracheal devices including a chamber as described herein, the endotracheal device comprises a third lumen extending from a third external port to an atomizing nozzle that is configured to deliver atomized fluid into the first lumen or the second lumen.

In one or more embodiments of the endotracheal devices including a chamber as described herein, the endotracheal device comprises a third lumen extending from a third external port to an atomizing nozzle that is configured to deliver atomized fluid to the bronchial bifurcation.

In one or more embodiments of the endotracheal devices including a chamber as described herein, the first lumen comprises a first one-way valve configured to allow inspiratory flow through the first lumen from the first external port to and out of the first internal port and limit expiratory flow through the first lumen from the first internal port to and out of the first external port.

In one or more embodiments of the endotracheal devices including a chamber as described herein, the second lumen comprises a second one-way valve configured to allow expiratory flow through the second lumen from the second internal port to and out of the second external port and limit inspiratory flow through the second lumen from the second external port to and out of the second internal port.

In another aspect, one or more embodiments of a transpulmonary thermal transfer system are described herein, the system including an optional endotracheal device configured for insertion through a tracheal passage to a location proximate the bronchial bifurcation, wherein the endotracheal device comprises: a tube extending between a proximal end and a distal end, wherein the distal end of the endotracheal device is configured for advancement to a location proximate the bronchial bifurcation through the tracheal passage; a first lumen extending through the endotracheal device, the first lumen extending from a first internal port to a first external port, wherein the first external port is proximate the proximal end of the endotracheal device, wherein the first external port positioned outside of the tracheal passage when the first internal port is positioned proximate the bronchial bifurcation; a second lumen extending through the endotracheal device, the second lumen extending from a second internal port to a second external port, wherein the second external port is proximate the proximal end of the endotracheal device, wherein the second external port is positioned outside of the tracheal passage when the second internal port is positioned proximate the bronchial bifurcation. The system further includes a breathing circuit apparatus configured to deliver heated fluid to the first external port of the first lumen of the endotracheal device and to remove fluid from the second external port of the second lumen of the endotracheal device, the breathing circuit apparatus comprising: a delivery lumen configured to deliver inspiration gas from a ventilator to the first external port of the first lumen; a primary heat exchanger configured to heat the inspiration gas in the delivery lumen to a first selected temperature; a vaporizer configured to deliver a selected liquid into the inspiration gas downstream from the primary heat exchanger, wherein the first selected temperature is at or above a boiling point of the selected liquid; and a condenser configured to trap selected liquid condensate in the delivery lumen before the selected liquid condensate reaches the first external port of the first lumen.

In one or more embodiments, the breathing circuit apparatus may include a control heat exchanger configured to adjust the inspiration gas to a delivery temperature in the delivery lumen downstream from the vaporizer and upstream from the first external port of the first lumen.

In one or more embodiments, the breathing circuit apparatus may include a removal lumen configured to remove expiration gas from the second external port of the second lumen and deliver the expiration gas to the ventilator.

In one or more embodiments, the breathing circuit apparatus may include an expiration gas condenser configured to trap selected liquid condensate in the removal lumen before the selected liquid condensate reaches the ventilator.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the insulated endotracheal devices, systems, or methods described herein. Rather, a more complete understanding of the invention will become apparent and appreciated by reference to the following Description of Illustrative Embodiments and claims in view of the accompanying figures of the drawing.

BRIEF DESCRIPTION OF THE VIEWS OF THE DRAWING

FIG. 1A is a graphic illustration of an exemplary configuration of the present invention as a dual lumen endotracheal tube.

FIG. 1B is a cross section taken along line 1B-1B of FIG. 1A.

FIG. 2A is a graphic illustration of a coaxial endotracheal tube configuration.

FIG. 2B is a cross section taken along line 2B-2B of FIG. 2A.

DESCRIPTION OF ILLUSTRATIVE EMBODIMENTS

Figure 1C:
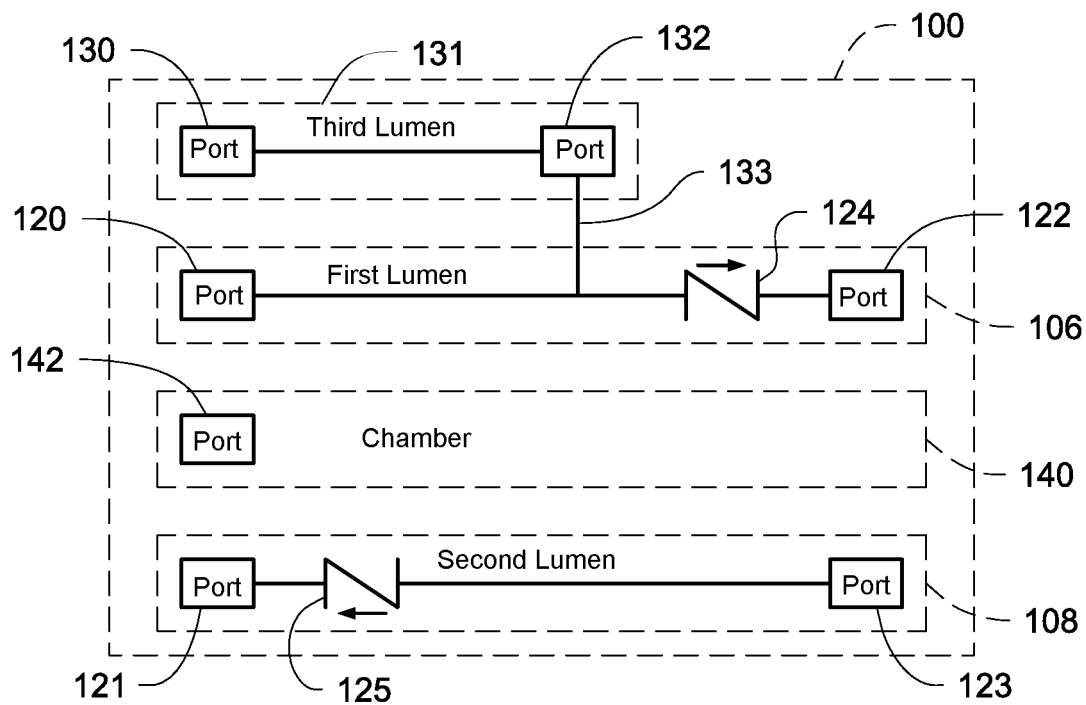
FIG. 1C is a schematic diagram of one illustrative embodiment of an endotracheal device as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

One illustrative embodiment of an endotracheal device as described herein is depicted in FIGS. 1A and 1B (with FIG. 1B being a cross-sectional view taken along line 1B-1B in FIG. 1A). The endotracheal (ET) device 100 as depicted in FIGS. 1A and 1B is configured for insertion through a tracheal passage to the bronchial bifurcation, i.e., the location at which the tracheal passage separates into left and right branches. The endotracheal device 100 is in the form of a tube that extends between a proximal end 107 and a distal end 109. The distal end 109 of the ET device 100 is configured for placement proximate the bronchial bifurcation.

The illustrative embodiment of the ET device 100 as depicted in FIGS. 1A and 1B includes a first lumen 106 extending through the endotracheal device 100. The first lumen 106 extends from a first internal port 122 to a first external port 120. The first external port 120 is proximate the proximal end 107 of the endotracheal device 100 and is, in one or more embodiments, configured for attachment to a gas transfer apparatus (not shown). The first external port 120 is positioned outside of the tracheal passage when the first internal port is positioned proximate the bronchial bifurcation as described herein.

The illustrative embodiment of the ET device 100 as depicted in FIGS. 1A and 1B also includes a second lumen 108 extending through the endotracheal device 100. The second lumen 108 extends from a second internal port 123 to a second external port 121. The second external port 121 is proximate the proximal end 107 of the endotracheal device 100 and is, in one or more embodiments, configured for attachment to a gas transfer apparatus (not shown). The second external port 121 is positioned outside of the tracheal passage when the second internal port 123 is positioned proximate the bronchial bifurcation as described herein.

In one or more embodiments, the endotracheal devices described herein include insulation 102 located in an interior of the tube of the endotracheal device 100 such that the insulation 102 is located between the first lumen 106 and the second lumen 108 to limit thermal energy transfer between fluids located in the first and second lumens.

In one or more embodiments of the ET devices as described herein, the first lumen 106 is separate and independent of the second lumen 108 such that fluid passing through the first lumen 106 cannot enter the second lumen 108 between the first external port 120 and the first internal port 122.

Referring to FIG. 1A, one illustrative embodiment of the endotracheal devices described herein is illustrated as the dual lumen endotracheal (ET) tube 100. Inspiratory arm 110 and expiratory arm 111 connect to the dual lumens 106 and 108 of the ET tube. An inflatable cuff 103 may be used to provide fixation for the tube once it has been inserted into a subject, and may also prevent the aspiration of gastric and oral contents into the lungs. That is, the cuff 103 could be inflated after insertion of the endotracheal tube 100 and deflated prior to extubation, and may also be used to provide physical separation between the ET tube and the tissue of the subject. Inflatable cuff 103 may be manually inflated by use of inflation port 104, such as with a syringe, or the inflation port 104 may be connected to a suitable pump system, such that manual pumping is unnecessary.

The illustrative embodiment of the ET device 100 as depicted in FIGS. 1A and 1B includes a first lumen 106 extending through the endotracheal device 100, wherein the first lumen 106 with an external surface located inside of the tube of the endotracheal device, which may be coated with an insulation layer located on the external surface of the first lumen 106. Second lumen 108 includes an external surface located inside of the tube of the endotracheal device, which may be coated with an insulation layer located on the external surface of the second lumen 108.

The dual lumen ET tube 100 limits or prevents mixing of the inspiratory and expiratory gases. In one or more embodiments, the insulation 102 between the lumens may limit thermal energy transfer between the cooled inspiratory gas and the warmed expiratory gases emanating from the lungs. By maintaining the inspiratory gas at the desired temperature, and preventing heat transfer from the subject's tissue, and the expired gas, hypothermia treatment can be achieved rapidly and efficiently.

In one or more embodiments, unidirectional flow valves (not pictured) may be coupled to the entrance of the inspiratory limb 110 and another unidirectional valve coupled to the exit of the expiratory limb 111 of the airway device to further prevent mixing of the gases. The first lumen 106 may include a first one-way valve configured to allow inspiratory flow through the first lumen from the first external port 120 to and out of the first internal port 122 and limit expiratory flow through the first lumen 106 from the first internal port 122 to and out of the first external port 120. The one-way valve may be located in the first lumen 106 closer to the first internal port 122 than the first external port 120. Alternatively, or additionally, the first one-way valve may located in the first lumen 106 closer to the first external port 120 than the first internal port 122.

In one or more embodiments, the second lumen 108 may include a second one-way valve (not pictured) configured to allow expiratory flow through the second lumen 108 from the second internal port 123 to and out of the second external port 121 and limit inspiratory flow through the second lumen 108 from the second external port 121 to and out of the second internal port 123. The second one-way valve may be located in the second lumen 108 closer to the second external port 121 than the second internal port 123. Alternatively, or additionally, the second one-way valve may be located in the second lumen 108 closer to the second internal port 123 than the second external port 121.

Insulation material 101 provides for limiting the heat transfer from the subject's tissue, and insulation material 102 provides for limiting the heat transfer from the expired gas to the cooled inspiratory gas. Insulation 101 and 102 may be flexible, in order to facilitate bending of the flexible ET tube. Insulation 101 and 102 may be of similar materials, which include any suitable material in the form of paint, foam, concentric sheets, or enclosed cells, ranging in thickness from a few microns to several millimeters.

Insulation 101 and 102 may be made of any biologically inert material such as polypropylene, polyurethane, or polyethylene. In one example, the R value may be in the range of 3 or higher or even 6 or higher. Here, R=Delta T/Q, which gives Q=Delta T/R), where Delta T is the temperature gradient between the inside and outside of the endotracheal tithe. In one example, Delta T may be 20° C., and with R around 5, the heat transfer rate would be around 20/5=4 watts per m2. By use of suitable insulation with higher R values (as with a silica Aerogel which is typically considered to have an R value of 10), Delta T may be 100° C. or more. The interior of the conduit or the first layer or the outer layer of external insulation 101 may be painted or otherwise coated with reflective material so as to minimize radiant heat loss or heat gain by fluids within the conduit. The entire length of the conduit in the airway may be insulated.

Another layer of effective insulation may be achieved by expanding the area of the inflatable cuff 103 to run along the entire length of ET tube 100. In this configuration, the cuff 103 could be made of similar material to the insulation 101 or 102. Inside the inflatable cuff 103, air, or other suitable gases, may be cooled or temperature controlled to aid as an insulating factor between the trachea and the gases flowing through the tube. Cuff 103 could also be inflated with an insulating material, or a combination of an insulating material and a gas. Alternatively, the inflatable cuff 103 may be modified, such as with a supporting structure (not shown), to contain a vacuum, which is an excellent insulator. In this configuration, the cuff 103 may be deployable in another fashion without the use of air pressure, which may be similar to the deployment of a nitinol stent. Deployment of such a stent would be familiar to those skilled in the art. The nitinol material structure may also provide support against the internal vacuum. In any configuration, once deployed, the pressure of the inflation would also tend to move the tube 100 into the center of the trachea further away from the warmth of the trachea.

FIG. 1C is a schematic diagram of the fluid handling components that may be found in one or more embodiments of an endotracheal device configured for insertion through a tracheal passage to the bronchial bifurcation as described herein. The endotracheal device 100 depicted schematically in FIG. 1C includes a first lumen 106 that, as described herein, extends through the endotracheal device 100. In one or more embodiments, the first lumen 106 extends from a first internal port 122 to a first external port 120. In one or more embodiments, the first external port 120 is proximate the proximal end of the endotracheal device 100 and configured for attachment to a gas transfer apparatus. In one or more embodiments, the first external port 120 is positioned outside of the tracheal passage when the first internal port 122 is positioned proximate the bronchial bifurcation as described herein.

The illustrative embodiment of FIG. 1C also includes a second lumen 108 extending through the endotracheal device 100. In one or more embodiments, the second lumen 108 extends from a second internal port 123 to a second external port 121. In one or more embodiments, the second external port 121 is proximate the proximal end of the endotracheal device 100 and configured for attachment to a gas transfer apparatus. In one or more embodiments, the second external port 121 is positioned outside of the tracheal passage when the second internal port 123 is positioned proximate the bronchial bifurcation as described herein.

In one or more embodiments, the first lumen 106 is separate and independent of the second lumen 108 such that gas passing through the first lumen 106 cannot enter the second lumen 108 between the first external port 120 and the first internal port 122.

In one or more embodiments of the endotracheal devices described herein, the endotracheal device 100 (as depicted in FIG. 1C) includes a third lumen 131 extending from a third external port 130 to an atomizing nozzle 132 that is configured to deliver atomized fluid into the first lumen 106 (through, e.g., lumen 133 as depicted) or into the second lumen 108. In one or more alternative embodiments, the endotracheal devices described herein may include a third lumen that extends from a third external port to an atomizing nozzle that is configured to deliver atomized fluid to the bronchial bifurcation without passing through either the first lumen 106 or the second lumen 108.

In one or more embodiments of the endotracheal devices described herein, the first lumen 106 may include a first one-way valve 124 configured to allow inspiratory flow through the first lumen 106 from the first external port 120 to and out of the first internal port 122 and limit expiratory flow through the first lumen 106 from the first internal port 122 to and out of the first external port 120. In one or more embodiments, the first one-way valve 124 may be located in the first lumen 106 closer to the first internal port 122 than the first external port 120. In one or more embodiments, the first one-way valve 124 is located in the first lumen 106 closer to the first external port 120 than the first internal port 122.

In one or more embodiments of the endotracheal devices described herein, the second lumen 108 may include a second one-way valve 125 configured to allow expiratory flow through the second lumen 108 from the second internal port 123 to and out of the second external port 121 and limit inspiratory flow through the second lumen 108 from the second external port 121 to and out of the second internal port 123. In one or more embodiments, the second one-way valve 125 may be located in the second lumen 108 closer to the second external port 121 than the second internal port 123. In one or more embodiments, the second one-way valve 125 may be located in the second lumen 108 closer to the second internal port 123 than the second external port 121.

Another optional feature depicted in FIG. 1C is the chamber 140 located between the first lumen 106 and the second lumen 108, with the chamber 140 serving as insulation between the lumens or in place of insulation between the lumens in one or more embodiments of the ET devices described herein. In one or more embodiments, the chamber 140 may be filled with any suitable fluid or combination of fluids, e.g., air, gas, liquid, etc. one or more embodiments, the chamber 140 may be a vacuum (i.e., contain one or more fluids held at a pressure below ambient pressure). In one or more embodiments of the endotracheal devices described herein, the chamber 140 may be located in an interior of the tube of the endotracheal device 100 between the first lumen 106 and the second lumen 108 and configured to limit thermal energy transfer between fluids located in the first and second lumens.

In one or more embodiments, the chamber 140 may include a vacuum port 142 proximate the proximal end of the endotracheal device 100 and configured for attachment to a vacuum device (not shown). In one or more embodiments, the vacuum port 142 may be positioned outside of the tracheal passage when the second internal port 123 is positioned proximate the bronchial bifurcation as described herein. In one or more embodiments, the chamber 140 comprises a structure configured to retain a space between the first lumen 106 and the second lumen 108 when the chamber 140 is held below atmospheric pressure. For example, the chamber 140 may define a rigid column located between the first and second lumens.

Figure 1D:
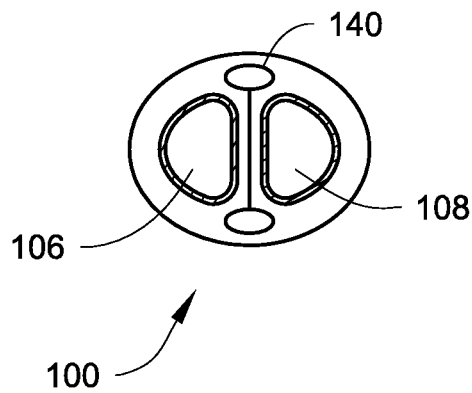
FIG. 1D is a cross-sectional view of another illustrative embodiment of an endotracheal device include an inflatable chamber between a pair of lumens.
Figure 1E:
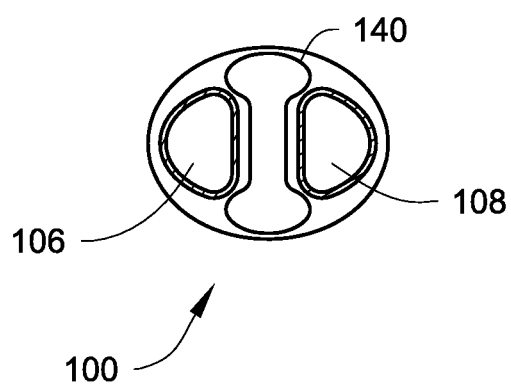
FIG. 1E is a cross-sectional view of another illustrative embodiment of an endotracheal device include a chamber separating a pair of lumens.

In one or more alternative embodiments of the endotracheal devices described herein, the chamber 140 may be in the form of an inflatable chamber that has, as depicted in FIG. 1D, a delivery configuration and an expanded configuration as depicted in FIG. 1E in which the chamber 140 provides more space between the first lumen 106 and the second lumen 140 than when the chamber 140 is in the delivery configuration. In one or more embodiments in which the endotracheal devices described herein includes an inflatable cuff positioned on an exterior of the tube (see, e.g., cuff 103 in FIG. 1A), the inflatable cuff may be in fluid communication with the chamber 140 such that when the chamber 140 is in the delivery configuration (FIG. 1D), the inflatable cuff is in the collapsed configuration and when the chamber 140 is in the expanded configuration (FIG. 1E) the inflatable cuff is in the inflated configuration.

Referring to FIG. 2A, a coaxial endotracheal tube configuration is illustrated. Here, inspiratory gas flow 220 depicts the flow into inspiratory limb 210, and expiratory gas flow 221 reflects the expired gas out of expiratory limb 211. In a similar fashion to FIG. 1A, inflatable cuff 203 is coupled with inflation port 204.

FIG. 2B is a cross section taken along line 2B-2B of FIG. 2A. This illustrative embodiment includes a first lumen 206, with an external surface located inside of the second lumen 208, and wherein insulation material 202 may be an insulation layer located on the external surface of the first lumen. The insulation 201 may be located on an external surface of the tube of the endotracheal device. Insulation material 201 and 202 may be located coaxially along the entire length of the ET tube. Also indicated in FIG. 2B are exemplary sizes for the inspiratory limb 210 at 6 mm, and expiratory limb 211 at 9 mm. These sizes are examples only, and other sizes may be used in order to decrease, or increase, the overall diameter of the endotracheal tub, or to maintain the same overall diameter, but to change the flow volume capability of the lumens by changing the diameter of the internal lumen only.

Figure 3A:
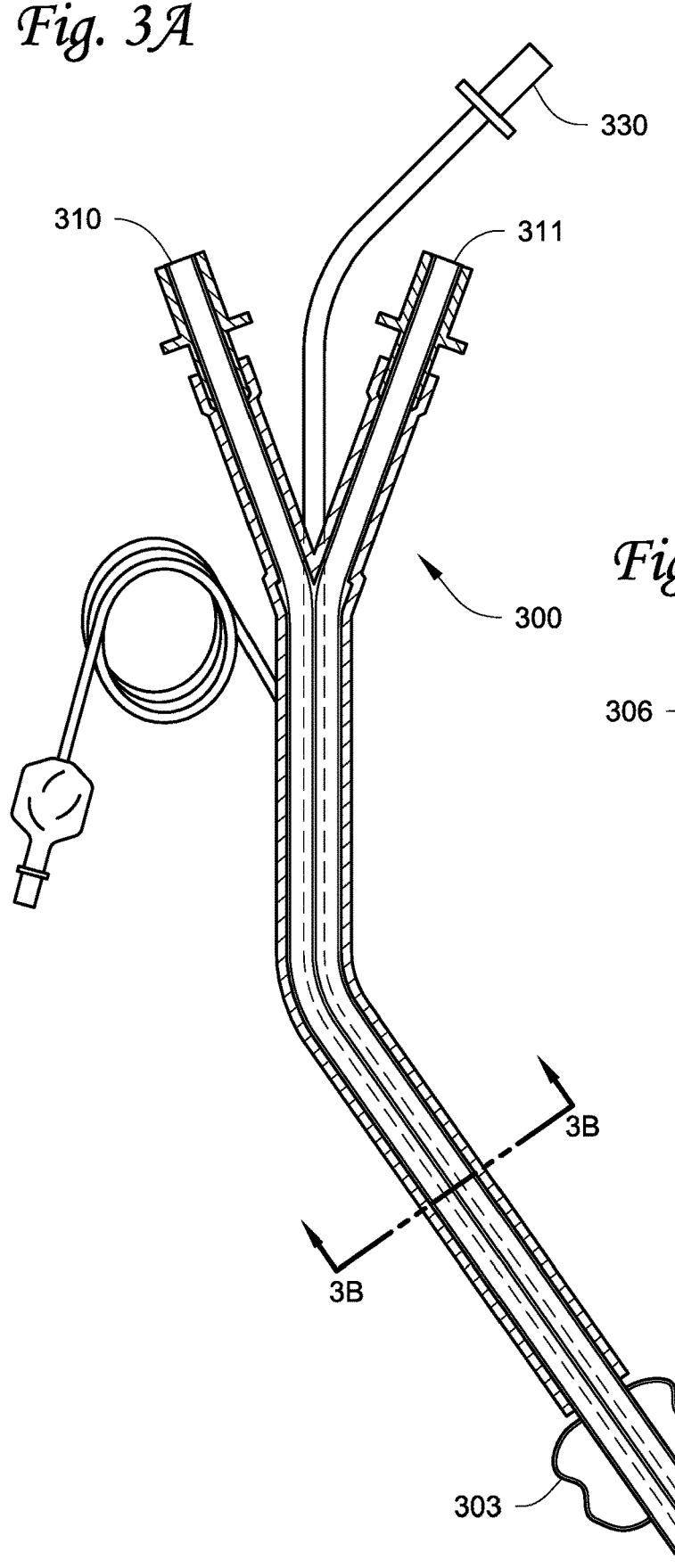
FIG. 3A is a graphic illustration of a multi-lumen endotracheal tube configuration.

Referring to FIG. 3A, a configuration for a multi-lumen endotracheal tube 300 is illustrated with inspiratory limb 310, expiratory limb 311, and with the addition of external port 330. External port 330 may allow for continuous or intermittent insufflation of fluids and/or gases. Port 330, in some configurations, may also be a working channel lumen that facilitates the insertion of tools or other devices at the distal end of tube 300 when needed, or may be configured to deliver atomized fluid.

Figure 3B:
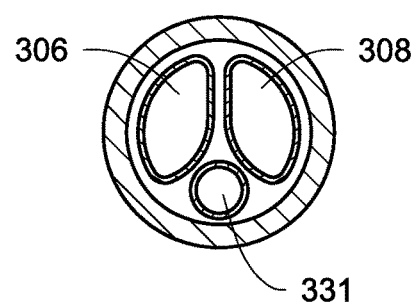
FIG. 3B is a cross section taken along line 3B-3B of FIG. 3A.

FIG. 3B is a cross section taken along line 3B-3B of FIG. 3A, which depicts the third lumen 331, which is connected to the external port 330, in location to the other lumens in the multi-lumen endotracheal tube 300.

The illustrative embodiment of the FT device 300 as depicted in FIGS. 3A and 3B may include a third lumen 331 extending from a third external port 330 to an atomizing nozzle (not shown) which may be configured to deliver atomized fluid into the first lumen 306 or the second lumen 308. In one configuration, the third lumen 331 extending from a third external port 330 to an atomizing nozzle, may be configured to deliver atomized fluid to a location proximate the bronchial bifurcation. In one or more embodiments, the ET device 300 may also include an inflatable cuff 303 as described herein in connection with other illustrative embodiments of ET devices.

The endotracheal devices described herein may be used with a wide variety of breathing circuits. Examples of some potentially suitable systems may be described in U.S. Pat. No. 6,983,749.

Figure 4:
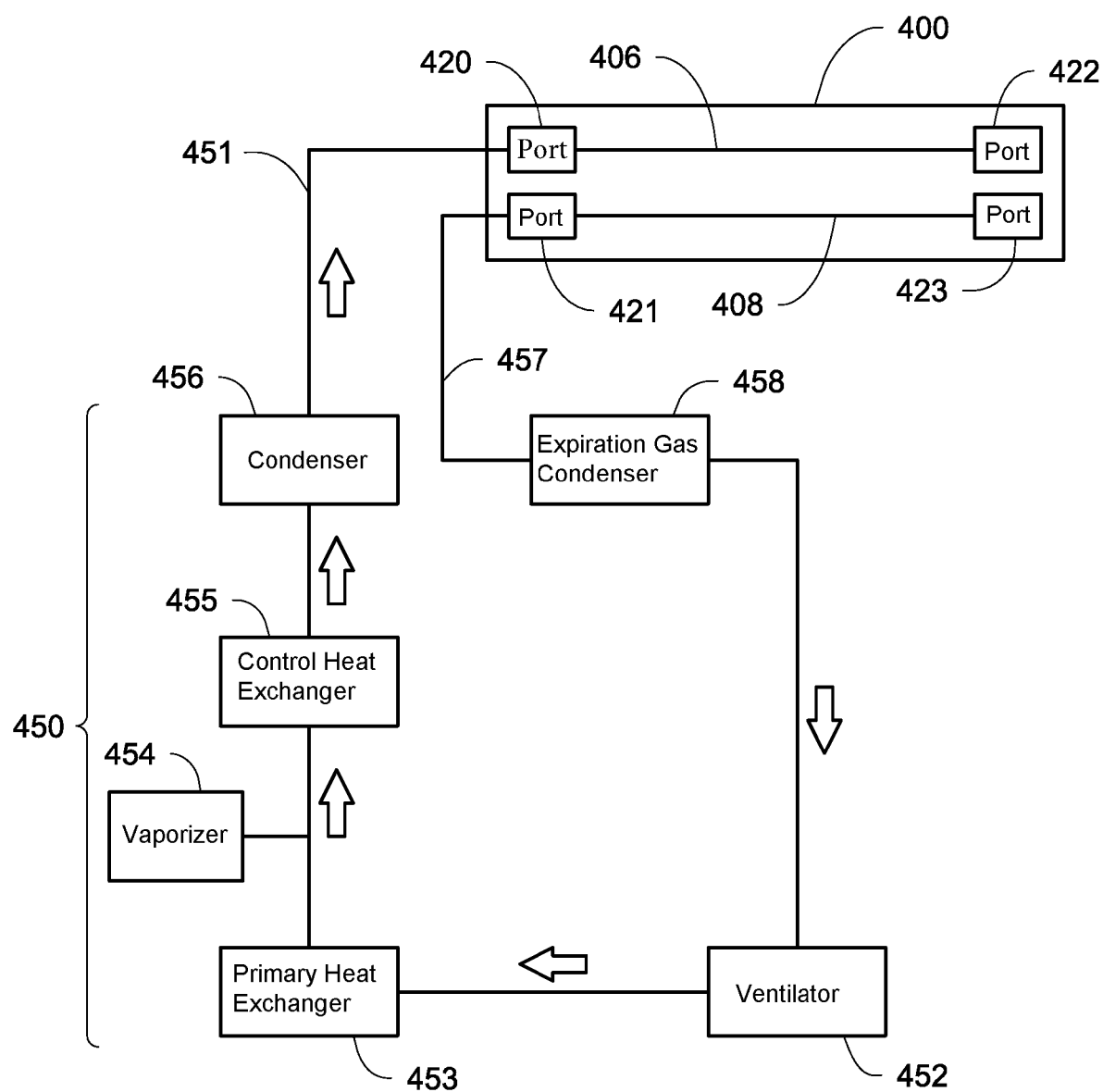
FIG. 4 is a schematic diagram of one illustrative embodiment of a transpulmonary thermal transfer system including an optional endotracheal device and a breathing circuit apparatus.

One illustrative embodiment of another breathing circuit in the form of a transpulmonary thermal transfer system that may be used with the endotracheal devices described herein is depicted in FIG. 4. The breathing circuit is depicted in FIG. 4 as attached to an endotracheal device 400, although it should be understood that in one or more embodiments, the other components in the system may be supplied separately from the endotracheal device 400. Although the endotracheal device may include insulation or other features found in the endotracheal devices herein, systems such as the system depicted in FIG. 4 may, in one or more embodiments, be used with other endotracheal devices.

The depicted endotracheal device 400 is configured for insertion through a tracheal passage to a location proximate the bronchial bifurcation and includes a tube extending between a proximal end and a distal end, wherein the distal end of the endotracheal device is configured for advancement to a location proximate the bronchial bifurcation through the tracheal passage. In or more embodiments, a first lumen 406 extends through the endotracheal device 400, the first lumen 406 extending from a first internal port 422 to a first external port 420. The first external port 420 is proximate the proximal end of the endotracheal device 400 and is positioned outside of the tracheal passage when the first internal port 422 is positioned proximate the bronchial bifurcation as described herein. The endotracheal device 400 also includes a second lumen 408 extending through the endotracheal device 400, the second lumen 408 extending from a second internal port 423 to a second external port 421. The second external port 421 is proximate the proximal end of the endotracheal device 400 and is positioned outside of the tracheal passage when the second internal port 423 is positioned proximate the bronchial bifurcation as described herein.

The endotracheal device 400 is depicted as attached to a breathing circuit apparatus 450 configured to deliver heated fluid to the first external port 420 of the first lumen 406 of the endotracheal device 400 and to remove fluid from the second external port 421 of the second lumen 408 of the endotracheal device 400.

The breathing circuit apparatus 450 may, in one or more embodiments, include a delivery lumen 451 configured to deliver inspiration gas from a ventilator 452 to the first external port 420 of the first lumen 406. The breathing circuit apparatus 450 as depicted in FIG. 4 may, in one or more embodiments, include a primary heat exchanger 453 configured to heat the inspiration gas in the delivery lumen 451 to a first selected temperature.

In one or more embodiments, the breathing circuit apparatus 450 may include vaporizer 454 configured to deliver a selected liquid into the inspiration gas in the delivery line 451 downstream from the primary heat exchanger 453. In one or more embodiments, the first selected temperature is at or above a boiling point of the selected liquid.

The breathing circuit apparatus 450 may, in one or more embodiments, include a condenser 456 configured to trap selected liquid condensate in the delivery lumen 451 before the selected liquid condensate reaches the first external port 420 of the first lumen 406.

In one or more embodiments, the breathing circuit apparatus 450 may include a control heat exchanger 455 configured to adjust the inspiration gas to a delivery temperature in the delivery lumen 451 downstream from the vaporizer 454 and upstream from the first external port 420 of the first lumen 406.

The breathing circuit apparatus 450 may, in one or more embodiments, include a removal lumen 457 configured to remove expiration gas from the second external port 421 of the second lumen 408 and deliver the expiration gas to the ventilator 452.

In one or more embodiments, the breathing circuit apparatus 450 may include an expiration gas condenser 458 configured to trap selected liquid condensate in the removal lumen 457 before the selected liquid condensate reaches the ventilator 452.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the insulated endotracheal devices, systems, or methods are discussed herein some possible variations have been described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. An endotracheal device configured for insertion through a tracheal passage to the bronchial bifurcation of a patient, the endotracheal device comprising a tube extending between a proximal end and a distal end, wherein the distal end of the endotracheal device is configured for placement proximate the bronchial bifurcation, the endotracheal device further comprising:

a first lumen extending through the endotracheal device, the first lumen extending from a first internal port to a first external port, wherein the first external port is proximate the proximal end of the endotracheal device and configured for attachment to a gas transfer apparatus, wherein the first external port is configured to be positioned outside of the tracheal passage when the first internal port is positioned proximate the bronchial bifurcation;

a second lumen extending through the endotracheal device, the second lumen extending from a second internal port to a second external port, wherein the second external port is proximate the proximal end of the endotracheal device and configured for attachment to a gas transfer apparatus, wherein the second external port is configured to be positioned outside of the tracheal passage when the second internal port is positioned proximate the bronchial bifurcation;

insulation located in an interior of the tube of the endotracheal device, the insulation being located between the first lumen and the second lumen to limit thermal energy transfer between fluids located in the first and second lumens, wherein the insulation comprises a chamber located in an interior of the tube of the endotracheal device, the chamber being located between the first lumen and the second lumen and configured to limit thermal energy transfer between fluids located in the first and second lumens, wherein the chamber comprises an inflatable chamber comprising a delivery configuration and an expanded configuration, and wherein the chamber provides more space between the first lumen and the second lumen in the expanded configuration than the delivery configuration; and an inflatable cuff positioned on an exterior of the tube, wherein the inflatable cuff is proximate the distal end of the endotracheal device, wherein the inflatable cuff comprises a collapsed configuration and an inflated configuration, wherein the inflatable cuff comprises a larger radial dimension in the inflated configuration than in the collapsed configuration where the radial dimension is measured radially outward from a longitudinal axis extending between the proximal end and the distal end of the tube, and wherein the inflatable cuff is in fluid communication with the chamber such that when the chamber is in the delivery configuration, the inflatable cuff is in the collapsed configuration and when the chamber is in the expanded configuration the inflatable cuff is in the inflated configuration;

wherein the first lumen is separate and independent of the second lumen such that gas passing through the first lumen cannot enter the second lumen between the first external port and the first internal port.

2. An endotracheal device according to claim 1, wherein the first lumen comprises an external surface located inside of the tube of the endotracheal device, and wherein the insulation comprises an insulation layer located on the external surface of the first lumen.

3. An endotracheal device according to claim 2, wherein the second lumen comprises an external surface located inside of the tube of the endotracheal device, and wherein the insulation comprises an insulation layer located on the external surface of the second lumen.

4. An endotracheal device according to claim 1, wherein the first lumen comprises an external surface located inside of the second lumen, and wherein the endotracheal device comprises an insulation layer located on the external surface of the first lumen.

5. An endotracheal device according to claim 1, wherein the insulation comprises tube insulation located on an external surface of the tube of the endotracheal device.

6. An endotracheal device according to claim 1, wherein the chamber comprises a vacuum port proximate the proximal end of the endotracheal device and configured for attachment to a vacuum device, wherein the vacuum port is configured to be positioned outside of the tracheal passage when the second internal port is positioned proximate the bronchial bifurcation, and wherein the chamber comprises a structure configured to retain a space between the first lumen and the second lumen when the chamber is held below atmospheric pressure.

7. An endotracheal device according to claim 1, wherein the endotracheal device comprises a third lumen extending from a third external port to an atomizing nozzle that is configured to deliver atomized fluid into the first lumen or the second lumen.

8. An endotracheal device according to claim 1, wherein the first lumen comprises a first one-way valve configured to allow inspiratory flow through the first lumen from the first external port to and out of the first internal port and limit expiratory flow through the first lumen from the first internal port to and out of the first external port.

9. An endotracheal device according to claim 1, wherein the insulation is configured to limit thermal energy transfer between a first fluid passing through the first lumen and a second fluid passing through the second lumen in the opposite direction such that the temperature of the first fluid does not change by more than 20 degrees Celsius when the first fluid and the second fluid are passing through each of the first and second lumens at flow rates of 50 liters per minute when the first and second fluids passing through the first and second lumens consist essentially of breathable gases and vapors.

* * * * *